United States Patent [19]

Langdon

[11] Patent Number: 4,556,472
[45] Date of Patent: Dec. 3, 1985

[54] COMPUTERIZED DEVICE FOR PULSED POTENTIAL VOLTAMMETRIC MEASUREMENT OF OXYGEN USING A MEMBRANCE COVERED POLAROGRAPHIC ELECTRODE

[75] Inventor: Christopher Langdon, Kingston, R.I.

[73] Assignees: Board of Governors for Higher Education, State of RI; Providence Plantations, both of Providence, R.I.

[21] Appl. No.: 625,134

[22] Filed: Jun. 27, 1984

Related U.S. Application Data

[62] Division of Ser. No. 369,474, Apr. 19, 1982, Pat. No. 4,464,230.

[51] Int. Cl.$^4$ ............................................. G01N 27/46
[52] U.S. Cl. ..................................... 204/406; 204/415
[58] Field of Search ................ 204/1 T, 400, 406, 415

[56] References Cited

U.S. PATENT DOCUMENTS 4,207,196  6/1980  Kunke ................................. 204/415

Primary Examiner—Andrew H. Metz
Assistant Examiner—Terryence Chapman
Attorney, Agent, or Firm—Thompson, Birch, Gauthier & Samuels

[57] ABSTRACT

An oxygen analyzer which measures the level of dissolved oxygen in a liquid stream. The measuring process embodies chronoamperoemetry of pulsed potential voltammetry. The signal from the electrode is real time averaged. The analyzer does not require temperature, salinity or pressure compensation circuitry and does not have to be calibrated repeatedly.

9 Claims, 3 Drawing Figures

COMPUTERIZED DEVICE FOR PULSED POTENTIAL VOLTAMMETRIC MEASUREMENT OF OXYGEN USING A MEMBRANCE COVERED POLAROGRAPHIC ELECTRODE

This is a division of application Ser. No. 369,474 filed Apr. 19, 1982, now U.S. Pat. No. 4,469,230.

BACKGROUND AND BRIEF SUMMARY OF THE INVENTION

The present invention relates to an apparatus and method for measuring the level of oxygen in a fluid stream.

Presently available devices for measuring dissolved oxygen in situ are subject to certain disabilities, the major disability being the requirement of calibrating the instrument or a daily basis.

It has been recognized that an oxygen sensor can be used with a measuring process known as chronoamperoemetry of pulsed potential voltammetry, first described by Lilley et. al., *J. Electronanal. Chem.*, 23 (1969) 426–429; see also Smart et. al., *In Situ Voltammetric Membrane Ozone Electrode, Anal. Chem.* Vol. 51, No. 14, Dec. '79, p. 2315-2319, and *Non-Steady State Measurement*, "The Measurement of Dissolved Oxygen", 1979.

In Lilley, the polarizing potential is applied as a pulse rather than a steady level. The pulse perturbs the sensor from equilibrium generating a large current transient which can be related to the oxygen partial pressure of the sample. Lilley recognized that this process had the important advantage over steady state measurements of increasing sensitivity and eliminating the requirement for stirring the sample solution as long as the current was read within four seconds of pulse application.

In spite of this teaching by Lilley in 1969, to date it is not believed that commercially available oxygen sensors embody the teachings of Lilley, but rather, that they use steady state measurements which measurements are subject to drift and the solution in which the electrode is immersed must be continually stirred to refresh the solution at the electrode surface.

The present invention provides a method and apparatus which electrochemically measures the quantity of a species in a fluid stream. More particularly, my invention provides a device wherein the acquisition, storage and generation of information corresponding to the oxygen level in a fluid stream is handled in a control module designed especially for that purpose.

Broadly, the invention comprises a sensor immersed in a fluid stream, the sensor specific for the species in the fluid stream to be measured, a switch to energize the sensor for a duration (d) and to prevent energization of the sensor for an interval (i); a circuit to real time average the signal from the sensor; an analog acquisition board and a computer adapted to control the activation of the switch, data acquisition and storage and all timing functions. In a preferred embodiment, temperature measurements are also derived from the sensor.

My invention achieves major economies in hardware using a microcomputer to control all important process parameters such as pulse duration, delay and repetition rate. Real time signal averaging is used to reduce the noise level and thereby improve precision. My device, when used for environmental sampling, does not require temperature salinity or pressure compensation circuitry.

The invention is particularly suitable for applications requiring long term measurements in environments where it is impracticable to service and recalibrate the sensor frequently, for example, industrial processes, such as fermentors, secondary sewage treatment plants and oceanorgraphic research. The major advantages of my invention are increased precision (changes as as small as 0.3 umolar can be detected, one time calibration) and the elimination of a stirring or flow rate requirement. The sensor is interfaced to the microprocessor, a complete record of time, temperature and oxygen concentration may be stored and made available for printout, plotting and statistical analysis.

DESCRIPTION OF THE PREFERRED EMBODIMENT

Hardware

Figure 1:
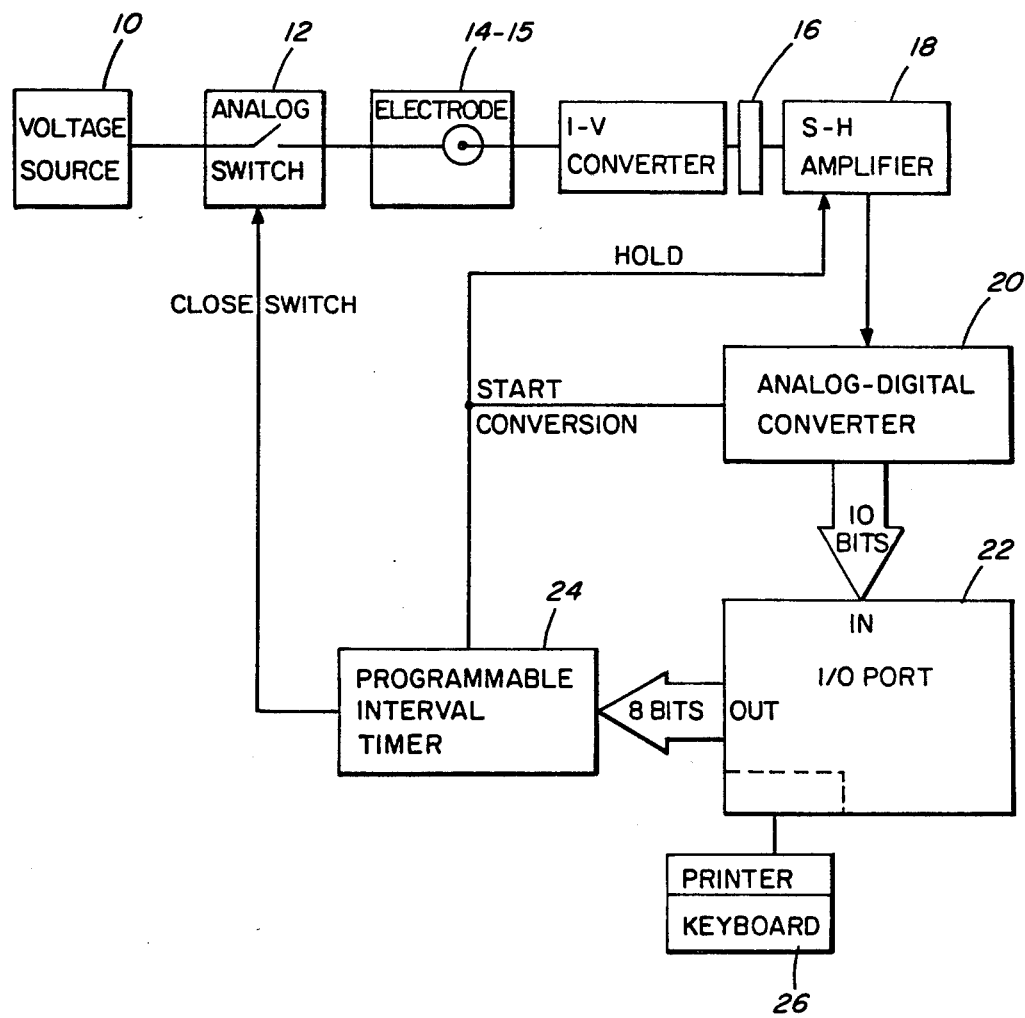
FIG. 1 is a block diagram of a system embodying the invention.

Referring to FIG. 1, a block diagram of an apparatus embodying the invention is shown and comprises a voltage source 10, which consists of a regulated power supply for a polarizing voltage; an analog switch 12 under computer control to generate a pulse and an electrode 14–15 of the Clark membrane type which transmits its output to a multiplexor 16. The electrode used is a YSI 5720 with a built-in thermistor. The output from the multiplexor 16 flows to a sample and hold circuit 18 and then to an A/D converter 20. A programmable interval timer 24 (as will be described) controls the switch 12, the sample and hold circuit and the A/D converter. A computer 22, which in the preferred embodiment is a TECHNICO 9990, interfaces with the A/D converter 20, the timer 24, and a keyboard printer 26 such as a TI ASR 33.

The Computer

The control of the computer is accomplished through instructions. The instructions are written to produce the desired sequence of operations and events. The computer thus has stored in its memory the programs or routines corresponding to each mode or operation desired of the computer. It is well known to those skilled in the art, that the computer comprises suitable controls, storage and computational units for performing the various arithmetic and logical functions on data which it processes in digital form. Any standard computer language consistent with the capability of the computer can be used for the instructions. All subroutines are not described in detail, since they can be written in any desired notations, formats or, depending upon the particular computer being utilized, computer language, (BASIC, FORTRAN) etc. Programs and instructions described are put in terms of structural flow. Where necessary and applicable for purposes of the invention, individual programs are described. For the specific computer of the preferred embodiment, the manufacturer's handbook sets forth the necessary preparations and steps for the loading and running of a program.

As is well known, programs are loaded into the microcomputer and for illustration purposes, the programs used herein are identified as 02INT, 02ELEC and 02

READ. After the programs have been loaded, the mesaurement process as controlled by O2ELEC is completely automated. The oxygen concentration and temperature are sampled under Interrupt control in background; during the data acquisition the computer can be put to any other use which the user may desire.

At any time during or after data acquisition, the user can examine the data which has already been collected by running the program "O2READ". This program takes the raw sensor readings and converts them to temperature in degrees Centigrade and oxygen concentration in micromoles per liter using the current calibration function stored on the diskette. When this program is run, even while data acquisition is underway, the time, temperature, oxygen concentration, and current rate of change of oxygen in inches per liter per hour will be printed out in real time as the measurements are made. The following is an example of the data generated.

TABLE I

| PULSE DURATION 1.49727 | | | O2READ sample output | |
|---|---|---|---|---|
| PULSE INTERVAL 300 | | | | |
| SALINITY 32.8 | | | | |
| START PRINTOUT | | | | |
| AT RECORD NO. 999 | | | | |
| CALIBRATION DATA | | | | |
| PROBE 1 = | | 9.371 | −2469.240 | |
| THERMISTOR TEMP = | | 146.611 | −22.249 | |
| TIME | TEMP | O2 µM | RATE µM/hr$^{-1}$ | MEAN |
| 27 | 12.033 | 15.2 | 227.9 | 0.00 | 639 |
| 28 | 12.117 | 15.2 | 227.9 | 0.00 | 639 |
| 29 | 12.200 | 15.2 | 227.9 | 0.00 | 639 |
| 30 | 12.283 | 15.2 | 227.9 | 0.00 | 639 |
| 31 | 12.367 | 15.2 | 227.5 | −0.94 | 639 |
| 32 | 12.450 | 15.2 | 227.5 | −1.41 | 639 |
| 33 | 12.533 | 15.2 | 227.5 | −1.41 | 639 |
| 34 | 12.617 | 15.2 | 227.5 | −0.94 | 639 |
| 35 | 12.700 | 15.2 | 227.5 | −0.01 | 639 |
| 36 | 12.783 | 15.2 | 227.5 | −0.01 | 639 |
| 37 | 12.867 | 15.2 | 227.5 | −0.01 | 639 |
| 38 | 12.950 | 15.2 | 227.5 | −0.01 | 639 |
| 39 | 13.033 | 15.2 | 227.5 | −0.01 | 639 |
| 40 | 13.117 | 15.2 | 227.5 | −0.01 | 639 |
| REINITIALIZE DATA PRINTER | | | | | |

Programs and instructions described below are put in terms of structural flow:

O2INT Structural Flow

1. Start
2. Input time (t) — time of day
3. Input duration (d) — pulse duration
4. Input interval (i) — interval between pulses
5. Timer 2 (24) interrupt in i seconds
6. R9 = the first position of entry in the data table established in the memory
7. Stop A graphic illustration of the data table is set forth below:

| DATA TABLE | | |
|---|---|---|
| | O2 | Temp. |
| R9 | 0 | 0 | 1 |
| R9+2 | 2 | 2 | 3 |
| R9+2 | 4 | 7 | 5 |
| R9+2 | n | n | n+1 |

O2ELEC Structural Flow

1. Interrupt request from step 4 of O2INT
2. Activate timer 2 of Programmable timer (24) to output a low going pulse on output line OUT2 in d seconds
3. Output CRU$_9$ high to close switch 12 thereby energizing the electrode circuit
4. Has OUT2 gone low yet? If no then hold. If yes:
5. Prepare to sample from electrode amplifier 18 by selecting channel 2 of multiplexer 16.
6. Execute BURST subprogram. This will sample the input repetitively at a specified rate until a specified no. of points have been acquired.
   (a) Specify no. of pts = 111
   (b) Specify rate as 3.3 KHz (0.3 milliseconds per point) therefore total sampling duration is 33.3 milliseconds which corresponds to 2 cycles of the major interfering noise frequency 60 Hz.
7. Average the 111 pts and store the result at the location pointed to by R9. (Real time averaging of the signal over 2 cycles of the 60 Hz noise very effectively filters out this source of noise.
8. Increment R9 by 1 to point to the next free location.
9. Output CRU$_9$ low to open switch 12 thereby de-energizing the electrode circuit.
10. Execute SCAN subprogram. This routine takes a single reading of the signal at a specified channel of multiplexor 16.
    (a) Specify channel 3 which monitors the temperature sensor 15.
11. Store the raw temperature sensor reading at the address pointed to by R9.
12. Is the data table full? If yet, Stop. If no:
13. Increment R9 by 1.
14. Activate timer 2 of programmable timer 24 to generate another interrupt request in i seconds.
15. Acknowledge interrupt request serviced by outputting a low going pulse on CRU$_6$ which will clear the interrupt request IRQ6 of FF−1.
16. Return from interrupt.

O2READ Structural Flow

1. Start
2. Input the answers to the following questions:
   (a) Salinity?
   (b) Start printout at record no.? (1–240) if 999 then then start printing the most current temperature and oxygen measurements.
3. Starting at the specified record no., calculate O$_2$ concentration and temperature from the raw sensor readings stored in the data table. These calculations are:

Temp °C. = 146.611 − 22.249 log$_e$ (raw temp sensor reading) From this in-situ temperature various quantities are calculated for the purpose of calculating temperature and salinity correction factors for converting the raw oxygen sensor readings to the desired concentration units. These are:

KELVIN = TEMP + 273.15
RT = 100./KELVIN
T100 = KELVIN/100.
*P1 = −173.249

*These constants are taken from a paper by Murray & Riley 1969 *Deep Sea Res.* 16,311.

P2 = 249.634
P3 = 143.348
P4 = −21.8492
P5 = −3.3096 × 10$^{-2}$
P6 = 1.4259 × 10$^{-2}$
P7 = 1.7 × 10$^{-3}$
A1 = P1 + P2*RT

A2 = P3 * $\log_e$(T100) + P4*T100
S1 = P5 + P6*T100 + P7*T100*T100
F = EXP(A1+A2+Salinity&S1)/EXP(A1+A2)
SLOPE = (1./EXP(9.371−2469.240*(1./KELVIN)*F
B1+ −15*SLOPE
O$_2$ concentration μM = B1+SLOPE*(raw O$_2$ sensor reading)
(Note: * equals times)

4. Print out data and also store in a diskette data file. Time, temp ° C., O$_2$ μM, Rate(μM hr$^{-1}$) continue until done or the BREAK is typed.
5. Enter menu of possible operations
   1. 02INT restarts data acquisition
   2. Plot of O$_2$ concentration vs. time
   3. Compute simple statistics, means, standard deviations, 95% confidence intervals, slope, intercept and correlation coefficient
   4. Update calibration data
   5. Print data

OPERATION

In the operation of the invention, an electrode 14-15 such as a Clark type membrane with thermistor is used in the preferred embodiment. The electrode 14-15 is inserted into the body of water, the oxygen level of which is to be measured. Whether inserted into a tank, bottle or the like is immaterial. For the data shown in Table I above, the water to be sampled was siphoned into a BOD bottle. The sensor, which had a taper the same as the ground glass neck of the bottle, was inserted carefully into the bottle so as not to trap any bubbles.

The following describes the operation of the invention with reference to the drawings.

The program 02INT is loaded into the computer 20 and the current time and pulse duration (d) and pulse interval (i) desired is input into the computer 22. In the specific example, the pulse duration was 1.5 seconds and the pulse interval was 5 minutes. The pulse duration could be any range depending upon the species in the fluid being measured and the characteristics of the membrane, including the recovery rate. For oxygen, a pulse duration from 0.5-3 seconds is suitable and a pulse interval of from 3-5 minutes or greater than five minutes is suitable.

Figure 2:
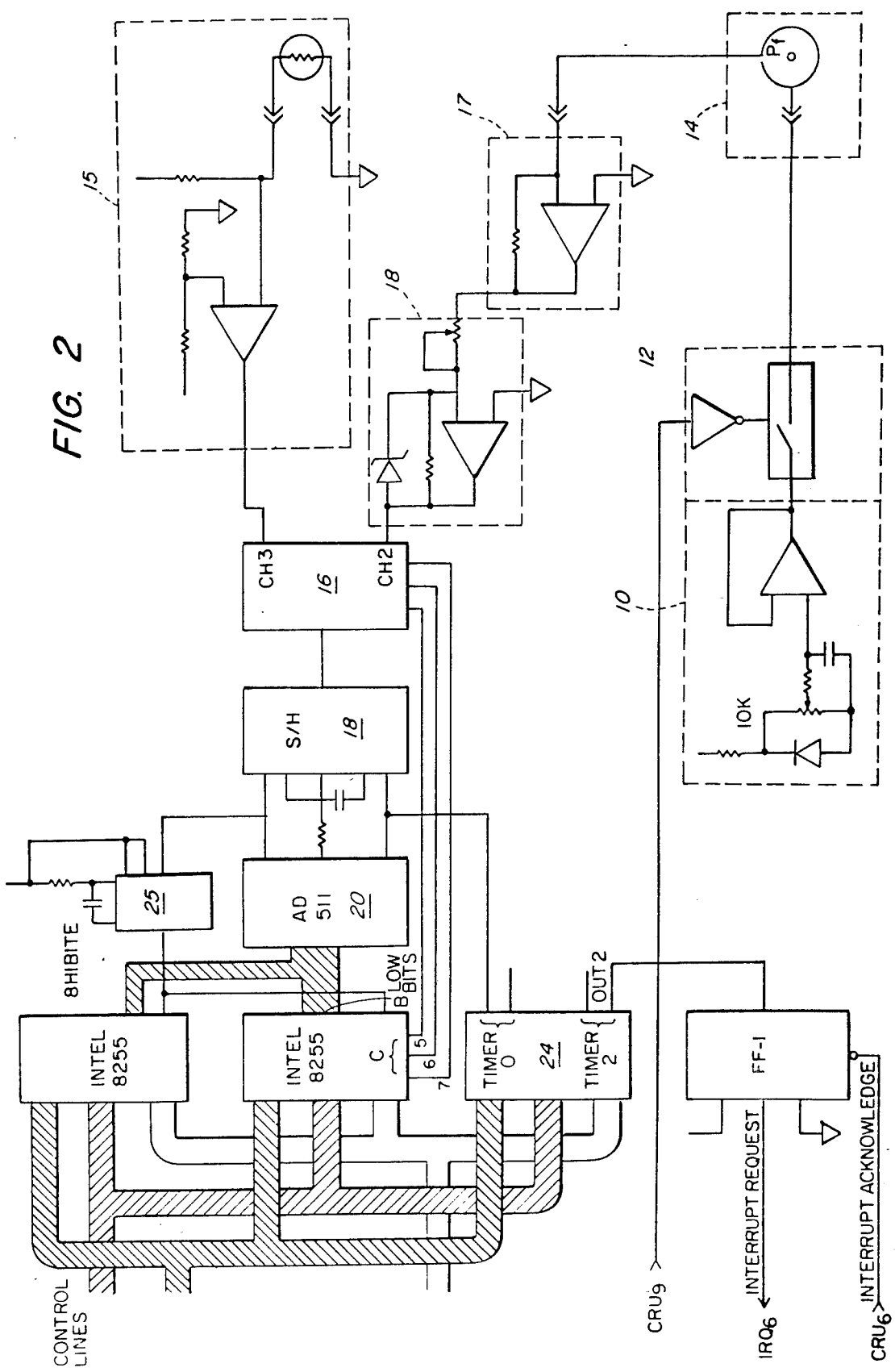
FIG. 2 is a schematic of the analog acquistion board and sensor circuit.
Figure 3:
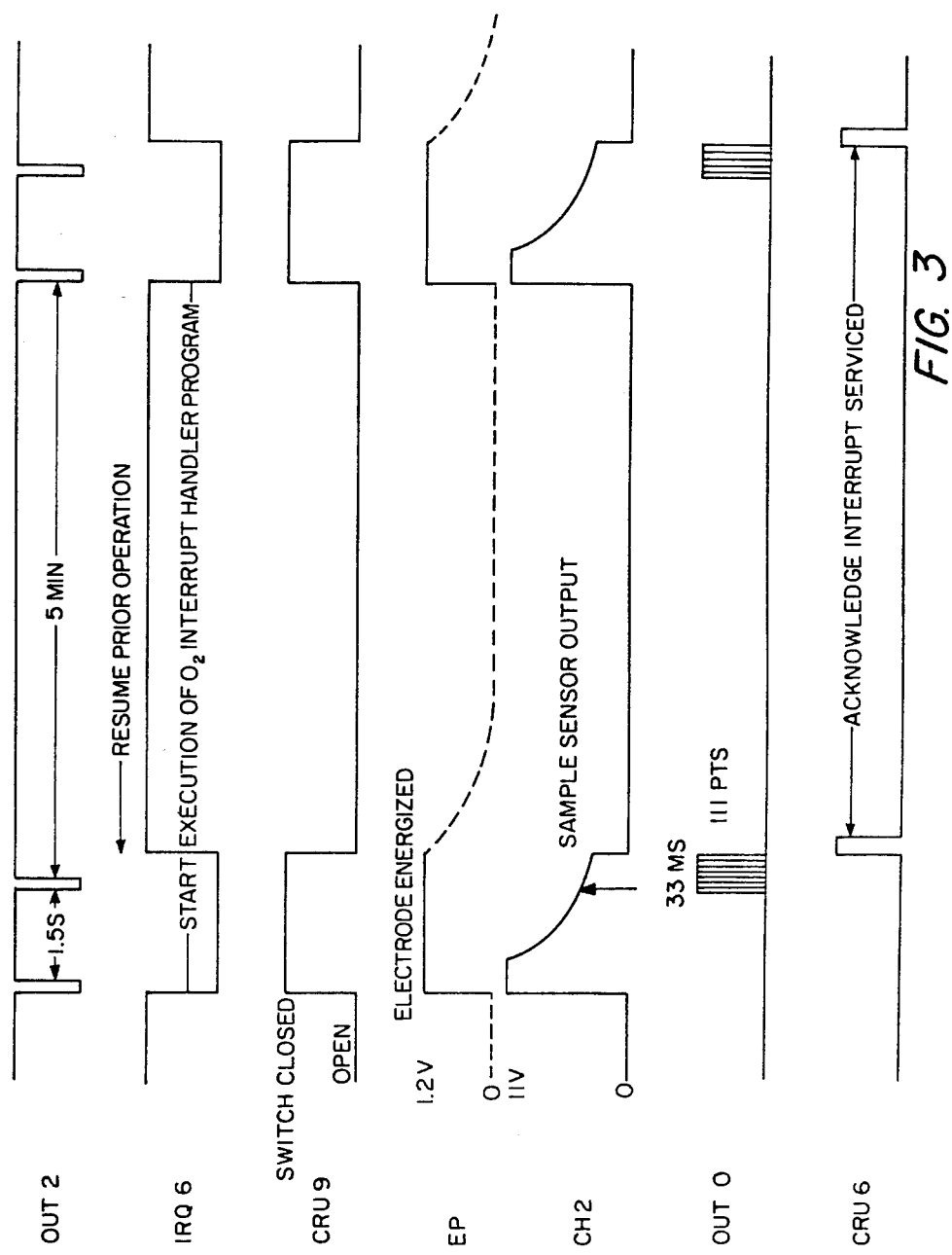
FIG. 3 is a timing diagram.

Referring to FIGS. 2 and 3, the computer data acquisition and process control is accomplished using two INTEL 8255 programmable peripheral devices. As shown in FIG. 2, these devices are organized as three READ/WRITE registers and a WRITE ONLY control register. To the computer 22, these registers appear as bytes of internal memory. Port B is programmed for strobed input and Port C is programmed for simple output. Ten Port B input lines 8 bits of 8255 lo and 2 bits of 8255 hi are connected to the output lines of the AD 571 analog to digital converter 20. A data ready pulse originating from the AD 571 latches the data from the AD 571 into the Port B input after being delayed 600 nanoseconds by monostable 25 to allow time for the data lines to settle. The falling edge of the data ready pulse also sets a bit in Port C of 8255 which doubles as a status register signifying that the input buffer is full. Software testing to see whether this bit is set can tell if new data is available in the input buffer. Reading the input, Port B, automatically clears the input buffer full flag.

The input of the analog to digital converter 20 is driven by the sample and hold amplifier 18. The sample and hold amplifier 18 tracks the input waveform from the multiplexer (16) until a convert command is issued to the sample and hold circuit via the OUT 0 line of programmable timer 24. At this time, the input voltage is held constant for 25μ seconds, the time it takes the converter 20 to make the analog to digital conversion.

The source of the input voltage to be sampled is selected by the multiplexer 16. The particular channel selected is determined by the data put out on the multiplexer address lines by bytes PC 5-7 of output Port C.

Channel 2 of the multiplexer 16 is connected to the oxygen sensor 14 and channel 3 is connected to the thermistor 15. The six other channels are available to monitor any other pertinent sensors as desired.

All time dependent data acquisition events are controlled by the INTEL 8253 programmable counter timer 24. The timer contains three completely independent timers, each operating on a different time base; two of which are used in this embodiment The input of Timer 0 is connected to a 1.5 Mhz time base and used to control the sampling rate of the analog to digital converter 20. The input of Timer 2 is connected to a 91.5 Hz time base and Timer 2 is used to generate interrupts after a 0.011–360 second delay. A pulse on the OUT2 line is generated when Timer 2 counts down to zero which toggles the output of a flip-flop FF-1 to low sending an interrupt request via IRQ$_6$ to the computer 22. If interrupts have been enabled, the 02ELECT program pointed to by the interrupt vector stored at location 18 will be executed, upon completion of the 02ELEC program the interrupt request is cleared by sending pulse out on the interrupt acknowledge line CRU$_6$.

Generation of a signal proportional to oxygen concentration begins with a well regulated power supply 10 which generates the polarizing voltage for the oxygen electrode 14. The analog switch 12 is in series with the oxygen electrode 14. The switch is opened and closed by computer control via CRU$_9$ so as to produce a pulse of precisely controlled duration (d). The height of the pulse is controlled by the 10K variable resistor and is set to put the electrode in the plateau region of its I-V curve. The preferred pulse height has been found to be 1.2 volts for a duration of 1.5 seconds, which produces optimal linerality and long term stability. The current transient produced when the electrode 14 is energized is converted to a proportional voltage by the operational amplifier 17. A second stage of amplification at 18 inverts the signal so that the voltage transient 0-10 V is positive. The eleven volt Zener diode clips signals which exceed 11 volts protecting the subsequent stages. The signal is input into the multiplexer channel 2.

A voltage divider circuit 15 converts the resistance changes in the thermistor 15 into a proportional voltage signal which is fed to channel 3 of the analog multiplexer 16. See flow chart.

FIG. 3 illustrates the timing sequence used in the preferred embodiment of my invention.

Although my invention has been described with reference to the measurement of oxygen, any species in a fluid stream, gaseous or ionic, may be measured.

Having described my invention, what I now claim is:
1. An apparatus for determining the level of oxygen in a fluid stream which comprises:
   (a) means to place an electrode in electrolytic communication with a fluid stream containing oxygen;
   (b) means to energize the electrode for a first duration of time (d) and to prevent energization of the electrode for an interval of time (i), which interval of time (i) is longer than the duration time (d), the electrode providing a first signal corresponding to the oxygen to be measured derived from time (d);

(c) means to sample repeatedly over at least one cycle of the predominant noise frequency the first signal generated from the electrode which signal corresponds to time (d), the first signal sampled at a rate over at least the one cycle of the predominant noise frequency such that the sampled signal when averaged provides a signal substantially free of drift;

(d) means to average the signals so sampled;

(e) means to store the signals so averaged;

(f) means to provide a second signal corresponding to the salinity of the fluid stream;

(g) means to input the value of the salinity into the apparatus;

(h) means to calculate salinity correction factors;

(i) means to apply the salinity corection factors to stored averaged signals to produce data corresponding to the level of the oxygen in the fluid stream being measured; and (j) computer means to control the energization of the electrode; and the sampling, averaging and storing of the signals; and the calculation of the salinity correction factors and the application of the correction factors to the averaged signals.

2. The apparatus of claim 1 which includes means to calculate and means to display the time rate of change of oxygen concentration using linear regression analysis.

3. The apparatus of claim 1 wherein the measns to energize the electrode includes means to apply a polarizing voltage to the electrode.

4. The apparatus of claim 1 which includes means to display the level of the oxygen in the fluid stream.

5. The apparatus of claims 1 or 4 wherein the means to average the signal so taken includes means to average the signal over at least two cycles of the predominant noise frequency.

6. The apparatus of claim 1 which includes:
means to provide a third signal which corresponds to the temperature of the fluid stream;
means to calculate temperature correction factors;
means to apply the temperature correction factor to the stored signals and wherein the computer means includes means to calculate the temperature correction factors and to apply said correction factors to the averaged signals.

7. The apparatus of claim 6 which includes:
means to calculate the temperature correction factors using nonlinear equations.

8. The apparatus of claim 6 which includes means to alternately select for sampling both the first and the third signals.

9. The apparatus of claim 8 which includes means to display simultaneously the level of the oxygen in the fluid stream and the temperature of the fluid stream.

* * * * *